United States Patent
Khosravi

(12) 
(10) Patent No.: US 6,361,546 B1
(45) Date of Patent: Mar. 26, 2002

(54) DEPLOYABLE RECOVERABLE VASCULAR FILTER AND METHODS FOR USE

(75) Inventor: Farhad Khosravi, San Mateo, CA (US)

(73) Assignee: Endotex Interventional Systems, Inc., Cupertino, CA (US)

( * ) Notice: Subject to any disclaimer, the term of this patent is extended or adjusted under 35 U.S.C. 154(b) by 0 days.

(21) Appl. No.: 09/483,272

(22) Filed: Jan. 13, 2000

(51) Int. Cl.$^7$ ................................................ A61B 17/00
(52) U.S. Cl. ...................................................... 606/200
(58) Field of Search .............................. 606/200, 114, 606/127, 159, 191, 1, 108, 192

(56) References Cited

U.S. PATENT DOCUMENTS

| | | | |
|---|---|---|---|
| 4,969,891 A | | 11/1990 | Gewertz |
| 5,626,605 A | | 5/1997 | Irie et al. |
| 5,669,933 A | | 9/1997 | Simon et al. |
| 5,800,525 A | | 9/1998 | Bachinski et al. |
| 5,836,968 A | | 11/1998 | Simon et al. |
| 5,893,869 A | | 4/1999 | Barnhart et al. |
| 5,928,261 A | | 7/1999 | Ruiz |
| 5,941,896 A | * | 8/1999 | Kerr ........................... 606/200 |
| 5,984,947 A | | 11/1999 | Smith |
| 6,007,558 A | | 12/1999 | Ravenscroft et al. |
| 6,027,520 A | | 2/2000 | Tsugita et al. |
| 6,152,946 A | | 11/2000 | Broome et al. |
| 6,179,857 B1 | * | 1/2001 | Bates et al. .................. 606/200 |

FOREIGN PATENT DOCUMENTS

| | | |
|---|---|---|
| FR | 2567405 | 1/1986 |
| WO | WO 99/23976 | 11/1997 |
| WO | WO 99 22673 A | 5/1999 |
| WO | WO 99 23976 A | 5/1999 |
| WO | WO 99 44510 A | 9/1999 |

OTHER PUBLICATIONS

PCT Publication No. WO 99/23976, "An Embolic Protection Device", May 20, 1999.

* cited by examiner

*Primary Examiner*—Kevin Truong
(74) *Attorney, Agent, or Firm*—Lyon & Lyon LLP

(57) ABSTRACT

A vascular filter is provided that includes a tubular member having proximal and distal ends, and a guidewire lumen. An expandable frame is attached to the tubular member capable of assuming collapsed and enlarged conditions, and filter material is attached to the frame, the filter material having an open proximal end when the frame assumes its enlarged condition. An apparatus for recovering a vascular filter from a blood vessel is also provided that includes a sheath and a retrieval member deployable from the sheath. The retrieval member includes a connector on its distal end for securing the tubular member, such as an expandable member within a recess for receiving the tubular member. The vascular filter may be constrained in its collapsed condition in a sheath, and the tubular member advanced over a guidewire to a location downstream of a treatment site. The, vascular filter is deployed and expanded to its enlarged condition across the blood vessel, the guidewire remaining in place. A procedure is performed at the treatment site, the vascular filter capturing released emboli. The retrieval device is advanced over the guidewire, the vascular filter is secured to the retrieval member, and the vascular filter and retrieval device are withdrawn from the blood vessel.

35 Claims, 4 Drawing Sheets

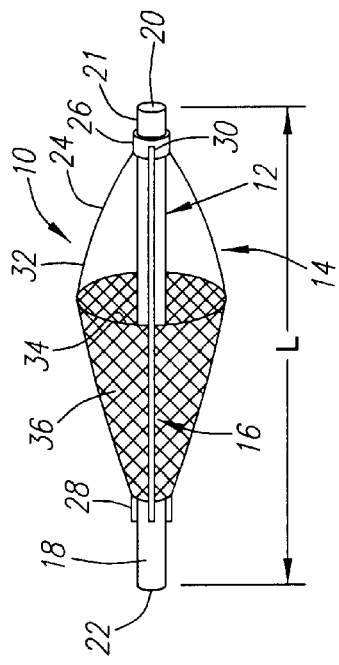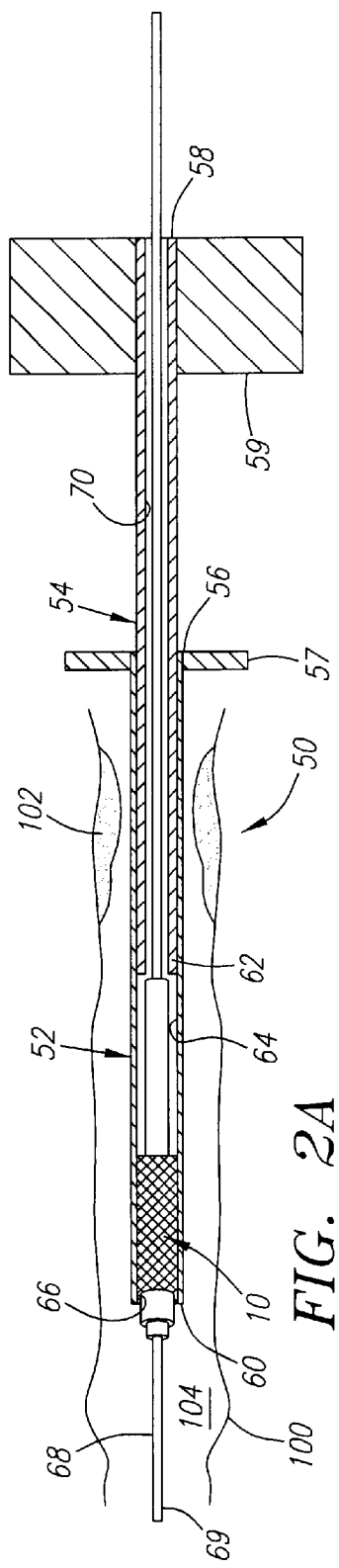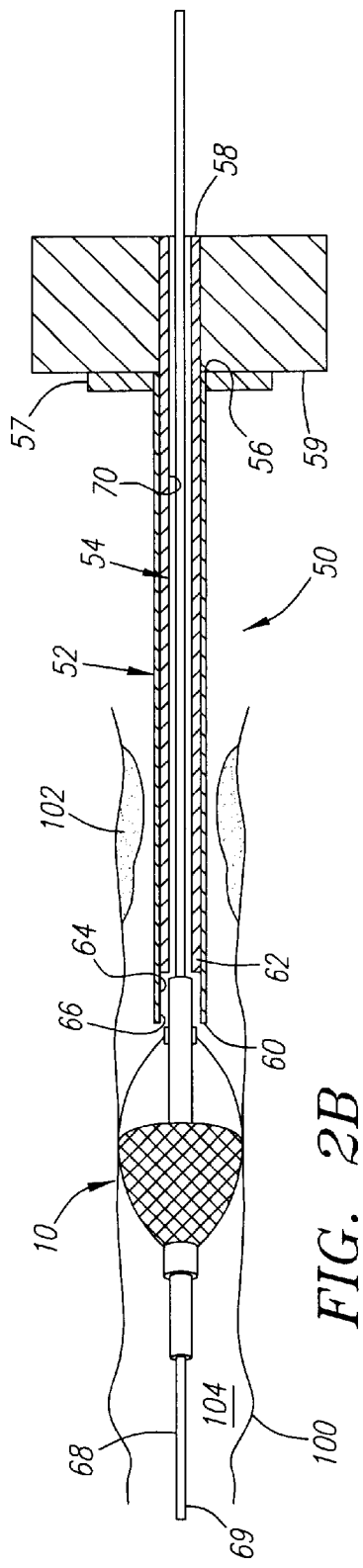
FIG. 1
FIG. 2A
FIG. 2B

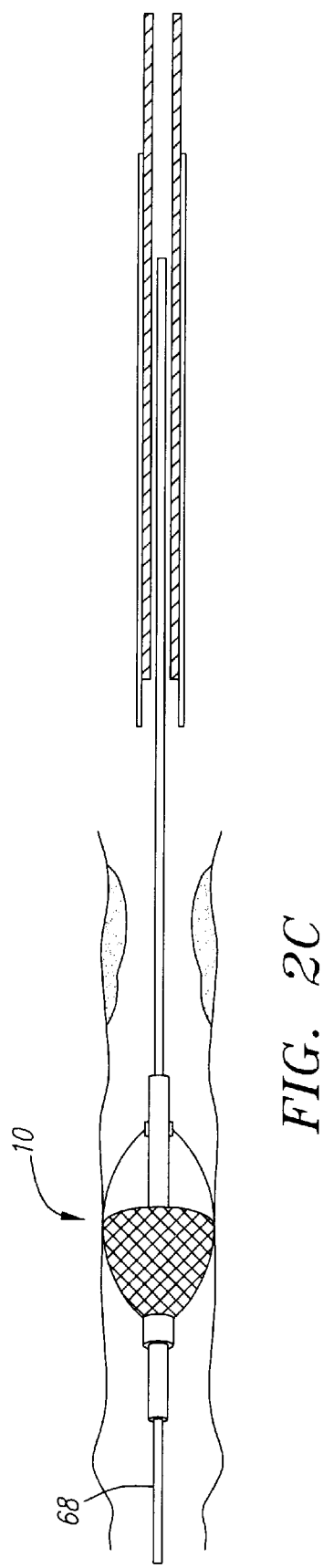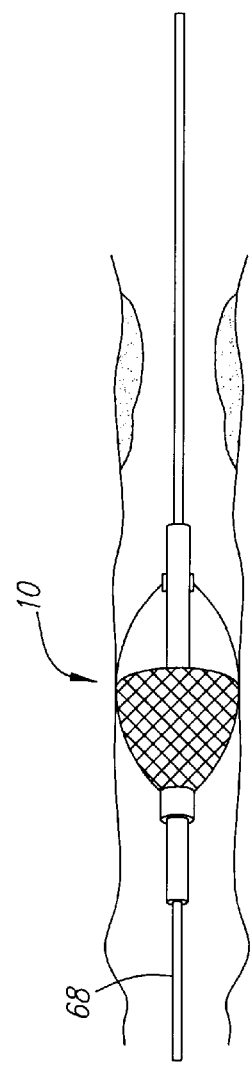

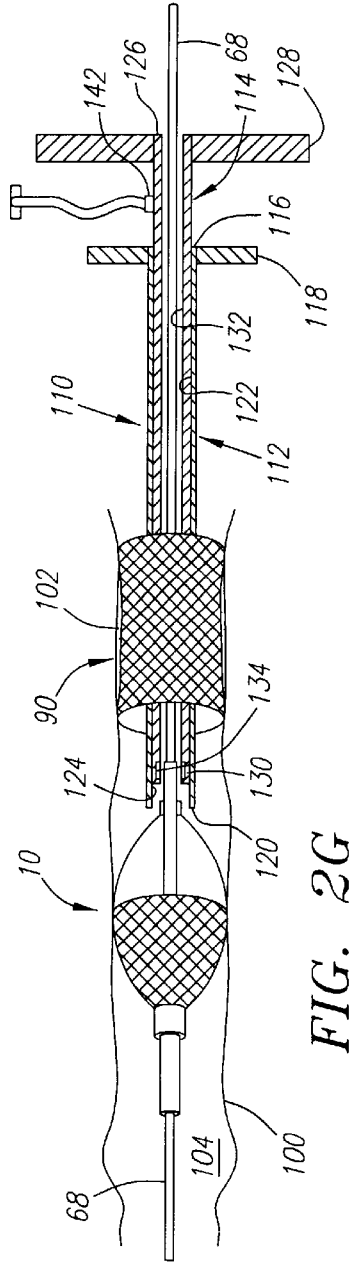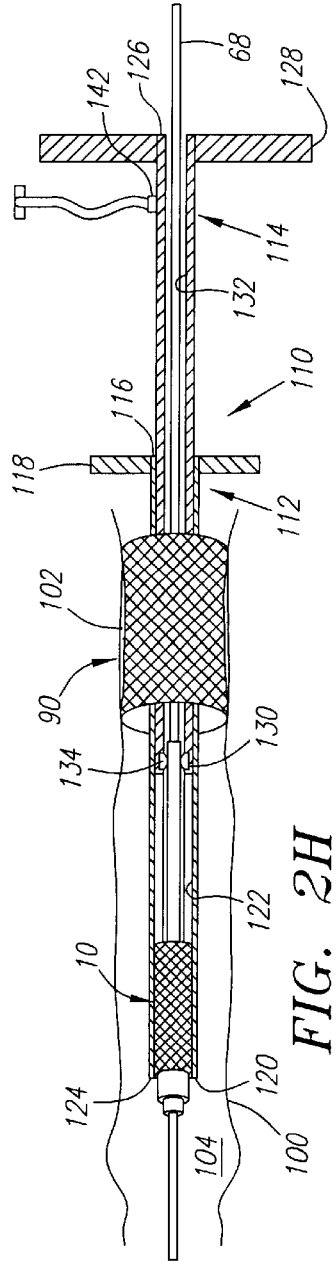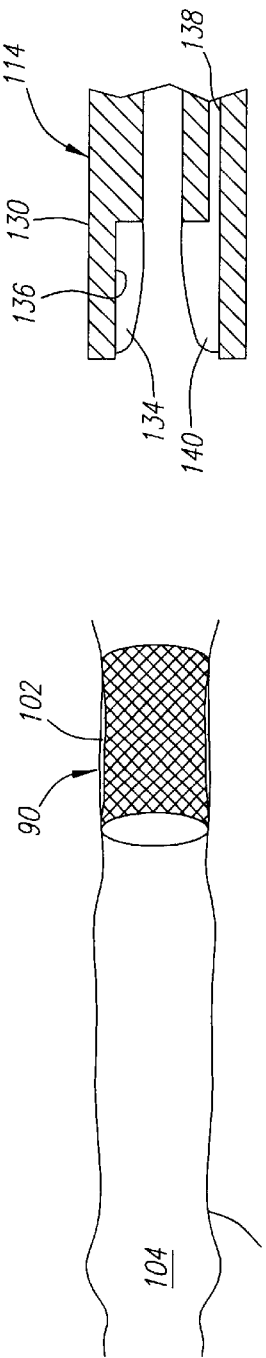

DEPLOYABLE RECOVERABLE VASCULAR FILTER AND METHODS FOR USE

FIELD OF THE INVENTION

The present invention relates generally to vascular filters, and more particularly to vascular filters that may be deployed within a blood vessel and subsequently recovered, and to apparatus and methods for filtering a blood vessel during an endovascular procedure using such filters.

BACKGROUND

A number of endovascular procedures are presently performed on patients with atherosclerotic disease and the like to treat stenotic or occluded regions within the patient's blood vessels, such as the coronary, carotid or cerebral arteries. For example, an angioplasty procedure may be used to dilate a stenosis, or an atherectomy may be performed to open severely occluded regions. A stent or other prosthesis may be implanted to retain patency of a vessel, either alone or in conjunction with these procedures.

One of the problems with these procedures, however, is that embolic material may be released from the wall of the vessel during the procedure, and travel downstream where it may become lodged or otherwise cause harm to the patient. For example, ischemic stroke may occur when such emboli are released in the carotid or cerebral arteries and travel to the patient's brain.

To prevent or minimize damage from emboli, vascular filters have been suggested that are generally mounted on a device, such as a catheter, a guidewire, or a sheath. These devices may be introduced within a blood vessel downstream of a location being treated, and the filter on the device deployed across the vessel to capture embolic material released during a procedure, such as one of the procedures above. Upon completion of the procedure, the filter is collapsed, and the device removed from the patient.

These filter devices are generally introduced endoluminally over a rail, such as a guidewire, that is also used subsequently to introduce one or more surgical tools or other devices used to perform the procedure. During the advancement of these subsequent devices, the rail may be pushed and pulled axially within the vessel, causing the deployed filter to move back and forth. This movement of the filter may damage the vessel intima, may release embolic material captured by the filter, and/or may damage the structure of the filter itself.

Implantable filter devices have also been suggested that may be deployed, expanded and released within vessels, such as vena cava filters. These filter devices may not recovered, or may remain within the vessel for extended periods of time, where they may eventually become obstructed with thromboses, clots, emboli and the like, and harm the patient.

Therefore, there is a need for a vascular filter that may be deployed to capture embolic material with minimal risk of damage to the vessel and patient and/or that may be may be more easily recovered from the patient.

SUMMARY OF THE INVENTION

The present invention is directed to vascular filters that may be reversibly deployed within a blood vessel and subsequently recovered, and to apparatus and methods for filtering a blood vessel using such filters. In accordance with one aspect of the present invention, a vascular filter is provided that includes a tubular member having a proximal end and a distal end, and including a lumen for receiving a guidewire therethrough. An expandable frame is attached to the tubular member, the expandable frame being capable of assuming a collapsed condition and an enlarged condition. Filter material is attached to the expandable frame, the filter material having an open proximal end when the expandable frame assumes its enlarged condition.

A connector may be provided on the proximal end of the tubular member for detachably securing the vascular filter to a delivery device. In a preferred form, the expandable frame includes a plurality of struts, each of the struts including an intermediate region biased to bow outward from the tubular member, the proximal end of the filter material being attached to the intermediate region.

The vascular filter may be incorporated into an apparatus for filtering a blood vessel that includes the vascular filter, a tubular sheath, and an elongate retrieval member. The tubular sheath has a proximal end, a distal end for insertion into a blood vessel, and a lumen having an outlet at the distal end. The lumen preferably has a size for slidably receiving the vascular filter therein when the expandable frame is in its collapsed condition.

The retrieval member has a distal end deployable from the distal end of the tubular sheath, and a connector on its distal end for securing the tubular member thereto. In a preferred form, the retrieval member includes a recess in its distal end, and the mechanical connector is an expandable member in the recess.

The apparatus may be used in a method for filtering a blood vessel during an endovascular procedure. A vascular filter, such as that described above, is provided that includes an expandable frame and filter material disposed on a tubular member, the expandable frame being constrained in a collapsed condition. The vascular filter may be provided within a lumen of a tubular sheath, the tubular sheath constraining the frame in its collapsed condition.

A guidewire is placed within a blood vessel across a treatment site with its distal end at a location downstream thereof. The tubular member is advanced over the guidewire, with the expandable frame in its collapsed condition, to the location downstream of the treatment site. The expandable frame is expanded to its enlarged condition to open the filter material across the blood vessel, the guidewire remaining slidable within the tubular member. For example, the expandable frame may be biased to assume its enlarged condition, and the expandable frame may expand automatically when the vascular filter is deployed from the lumen of the tubular sheath.

An endovascular procedure may be performed at the treatment site, the vascular filter capturing embolic material released during the procedure. The procedure may involve advancing one or more surgical instruments or other devices over the guidewire. A retrieval member is then advanced endovascularly to the location downstream of the treatment site, preferably over the guidewire. The vascular filter is secured to the retrieval member, and the vascular filter and retrieval member are withdrawn from the blood vessel. Preferably, the expandable frame is directed to its collapsed condition before withdrawing the vascular filter and retrieval member from the blood vessel. For example, the retrieval member may include a tubular sheath having a lumen therein, and the expandable frame may be directed to its collapsed condition by withdrawing the vascular filter into the lumen of the tubular sheath.

Preferably, the tubular member is secured to the retrieval member with a mechanical connector on the retrieval member, such as the recess and expandable member described above. The retrieval member is manipulated until the proximal end of the tubular member is received in the recess, and then the expandable member is expanded to constrict the recess and thereby engage the proximal end of the tubular member. Alternatively, the mechanical connector may be a shrinking collar or collet device provided on the end of the retrieval member, that may grab the tubular member, for example, by receiving the tubular member in the collar and then reducing the collar diameter to secure the tubular member to the retrieval member.

An important feature of the present invention is that the vascular filter, when deployed within a blood vessel, slidably engages the guidewire used to deliver it. When subsequent devices are advanced over the guidewire, they may cause the guidewire to move back and forth within the vessel, but may not affect the deployed vascular filter, as the guidewire may simply slide back and forth within the tubular member. Thus, this slidable arrangement substantially reduces the risk of damage to the vessel that may be caused by inadvertent movement of the deployed vascular filter, as well as reducing the risk of damage to the filter itself.

Further, because the guidewire remains within the tubular member during the procedure, a retrieval device may be easily introduced into the vessel to recover the vascular filter. There is no need to hunt around within the vessel to locate the vascular filter, as the retrieval device may simply be advanced over the guidewire and into proximity with the vascular filter, thereby facilitating its withdrawal from the patient's body.

Other objects and features of the present invention will become apparent from consideration of the following description taken in conjunction with the accompanying drawings.

BRIEF DESCRIPTION OF THE DRAWINGS

FIG. 1 is a perspective view of a preferred embodiment of a vascular filter, in accordance with the present invention.

FIGS. 2A–2D are cross-sectional views, showing the vascular filter of FIG. 1 being deployed in a blood vessel downstream of a treatment site.

FIGS. 2G–2I are cross-sectional views of the blood vessel of FIGS. 2A–2D, showing the vascular filter being recovered and removed from the vessel, with the stent remaining in place across the treatment site.

FIG. 3 is a cross-sectional detail of a distal end of a retrieval member, showing an inflatable mechanical actuator for securing and recovering a vascular filter.

DETAILED DESCRIPTION OF THE PREFERRED EMBODIMENTS

Figure 2E:
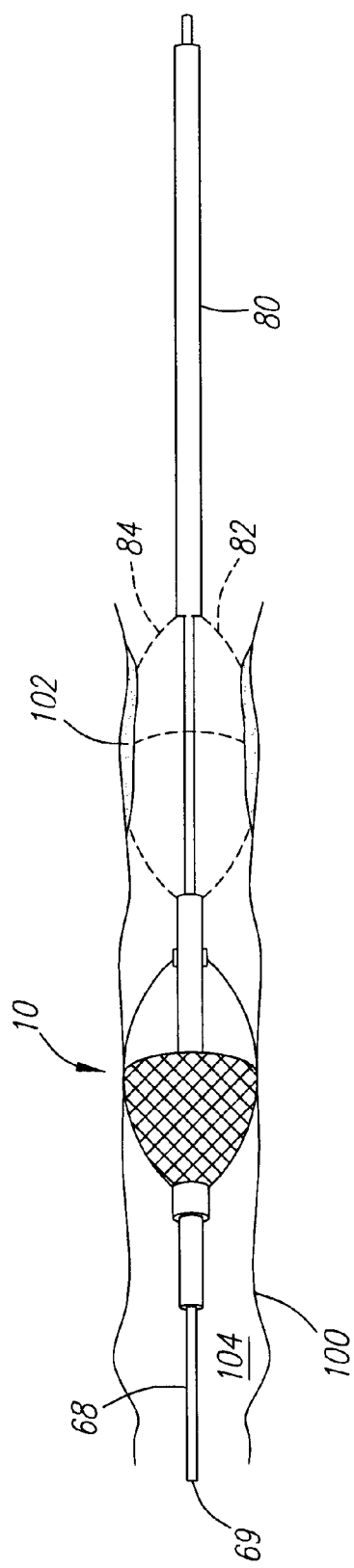
FIG. 2E is a cross-sectional view of the blood vessel of FIGS. 2A–2D, showing an angioplasty balloon being advanced therein for dilating the treatment site.

Turning now to the drawings, FIG. 1 shows a preferred embodiment of a vascular filter 10 in accordance with one aspect of the present invention. The vascular filter 10 generally includes an elongate tubular member 12, an expandable frame 14 disposed on the tubular member 12, and filter material 16 attached to the expandable frame 14 and/or the tubular member 12.

The tubular member 12 is preferably a section of substantially rigid cylindrical tubing having an outer surface 18,
a lumen 20 extending between its proximal and distal ends 21, 22, and a relatively short length L. Preferably, the length L of the tubular member 12 is sufficiently long to facilitate attachment of the expandable frame 14 to it, while being sufficiently short to facilitate introduction into and advancement along a body passage, such as a blood vessel. In a preferred form, the tubular member 12 is a section of hypotube having a length L of between about 5–50 mm, and an outer diameter of not more than about 25 mm, and more preferably between about 0.5–2.5 mm. The lumen 20 preferably has a diameter of at least 0.4 mm to facilitate the insertion of standard guidewires freely through the tubular member 12. The tubing may also be articulated at one or more points (not shown), thereby providing multiple lengths of tubing connected by articulations to provide transverse flexibility for the vascular filter 10.

The expandable frame 14 includes a plurality of struts or splines 24 having proximal and distal ends 26, 28 capable of assuming a collapsed condition (see FIG. 2A) and an enlarged condition, shown in FIG. 1. Preferably, the distal ends 28 of the struts are attached to the outer surface 18 of the tubular member, and the proximal ends 26 are attached to an annular collar 30 that is slidable on the tubular member 12. Alternatively, the distal ends 28 may be attached to a collar (not shown) and/or the proximal ends 26 may be attached directly to the outer surface 18 of the tubular member.

The struts 24 preferably are biased to expand towards the enlarged condition such that an intermediate region 32 is biased to bow outward from the tubular member 12, as shown in FIG. 1. The struts 24 may be directed against the outer surface 18 of the tubular member 12 to assume the collapsed condition, causing the collar 30 to slide proximally on the tubular member 12 in order to prevent buckling of the struts 24. Alternatively, if both ends 26, 28 of the struts 24 are fixed to the tubular member, the struts 24 may be twisted circumferentially about the outer surface 18 to facilitate directing them to the collapsed condition.

When not constrained in the collapsed condition, the struts may automatically expand to the enlarged condition, causing the collar 30 to slide distally along the tubular member 12. In a preferred form, the struts 24 may be formed from Nitinol or other shape memory alloy. The struts 24 may be formed from wire elements having a diameter of between about 0.075–0.25 mm, or flat bands having a width of between about 0.5–2.0 mm and a thickness of between about 0.05–0.25 mm, and the like.

The filter material 16 may be a woven fabric, wire frame or other known structure that may be attached to the struts 24 and/or to the outer surface 18 of the tubular member 12. For example, filter material having a pore size of at least about 0.05–0.30 mm, and more preferably about 0.15 mm may be provided to capture embolic material that is large enough to cause substantial risk of harm to the patient. The filter material 16 may be a polymeric sheet, such as polyethylene, with holes provided therein, for example, by drilling, or a thin metal sheet with holes provided therein, for example, by laser drilling.

A distal end 36 of the filter material 16 is preferably attached to the outer surface 18 of the tubular member 12 and/or to the expandable frame 14 to substantially enclose the distal end 36. The filter material 16 includes an open proximal end 34 when the expandable frame 14 is in its enlarged condition, thereby defining a pocket 36 within the filter material 16 for capturing embolic material. The proximal end 34 may be supported by the intermediate region 32 of the struts 24, may be self-supporting, or may include a wire or similar loop frame (not shown). When the expandable frame 14 is directed to its collapsed condition, the proximal end 34 of the filter material 16 is substantially closed such that any embolic material captured in the pocket 36 is trapped therein.

Turning to FIGS. 2A and 2B, a preferred embodiment of a device 50 for delivering the vascular filter 10 within a blood vessel of a patient is shown. The delivery device 50 generally includes an elongate tubular sheath 52 and an elongate bumper member 54 slidably disposed within the sheath 52.

The sheath 52 is preferably formed from a flexible tubular body including a proximal end 56 with a finger grip or handle 57 and a distal end 60 having a side and shape for facilitating insertion within a blood vessel. A lumen 64 extends axially between the proximal and distal ends 56, 60 that has a diameter for slidably receiving the vascular filter 10 in its collapsed condition therethrough. Alternatively, the lumen 64 may have an enlarged distal region (not shown) for receiving the vascular filter 10 therein proximate an outlet 66 of the lumen 64, and a narrow proximal region (also not shown) for receiving the bumper member 54 and/or a guidewire 68 therethrough, as described further below.

The bumper member 54 is preferably formed from a flexible or semi-rigid tubular body having a substantially flat distal end 62, a proximal end 58 with a handle 59, and a lumen 70 for receiving a guidewire 68 therethrough. The bumper member 54 preferably has an outer diameter substantially smaller than the lumen 64 of the sheath 52 such that the bumper member 54 may be slidably received therein. Instead of a flat distal end 62, the bumper member 54 may include a connector (not shown) on the distal end 62 for detachably securing the proximal end 21 of the vascular filter 10 to the bumper member 54.

In a preferred form, the sheath 52 has an outer diameter of about 1.0–7.0 mm, an inner lumen diameter of about 0.5–6.0 mm, and a length of about 50–250 cm. The corresponding bumper member 54 may have an outer diameter of about 0.5–6.0 mm, an inner lumen diameter of about 0.4–1.0 mm, and a length of about 50–250 cm. The lengths of the sheath 52 and bumper member 54 are preferably substantially similar such that when their handles 57, 59 abut one another, the distal end 62 of the bumper member 54 is disposed proximate the outlet 66 of the sheath 52 to facilitate deployment of the vascular filter 10.

To prepare the delivery device 50 for use in an endovascular procedure, the vascular filter 10 is advanced into the lumen 64 of the sheath 52 until its distal end 22 is located proximate the outlet 66. The vascular filter 10 is preferably introduced into the lumen 64 from the proximal end 56 of the sheath 52, and then the distal end 62 of the bumper member 54 is inserted behind it, and advanced distally, pushing the vascular filter 10 into position proximate the outlet 66. This may facilitate constraining the expandable frame 14 in its collapsed condition and/or minimize the risk of damage to the struts 24 or filter material 16. Alternatively, the vascular filter 10 may be directed to its collapsed condition and inserted directly into the outlet 66 until fully received within the lumen 64. The bumper member 54 may then be inserted into the proximal end 56 of the sheath 52 until the distal end 62 of the bumper member 54 is in close proximity to the vascular filter 10.

To deploy the vascular filter 10 within a blood vessel, a guidewire 68 or other rail is initially placed across a treatment site 102 within a blood vessel 100, for example, using conventional percutaneous methods. Preferably, the distal end 69 of the guidewire 68 is positioned at a location downstream of the treatment site 102. The sheath 52, with the vascular filter 10 therein, is then advanced over the guidewire 68 until the distal end 60 of the sheath 52 extends beyond the treatment site 102, as shown in FIG. 2A. The bumper member 54 is then advanced, for example, by directing the handles 57, 59 towards one another, thereby pushing the vascular filter 10 through the outlet 66 and into the vessel 100.

Preferably, as shown in FIG. 2B, the expandable frame 14 of the vascular filter 10 automatically expands to its enlarged condition upon deployment from the sheath 52, thereby opening the proximal end 34 of the filter material 16 across the vessel 100. With the guidewire 68 disposed within the tubular member 12 of the vascular filter 10, the guidewire 68 may freely slide axially without disturbing the deployed vascular filter 10.

As shown in FIG. 2E, an angioplasty catheter 80 may then be advanced over the guidewire 68 until its distal end 82 extends through the treatment site 102 and an inflatable balloon 84 (shown in phantom) or other expandable member (not shown) on the catheter 80 is positioned across the treatment site 102. The balloon 84 may then be inflated, possibly several times, to engage and dilate the treatment site 102, as is known in the art. The balloon 84 is then deflated, and the catheter 80 withdrawn from the patient.

Figure 2F:
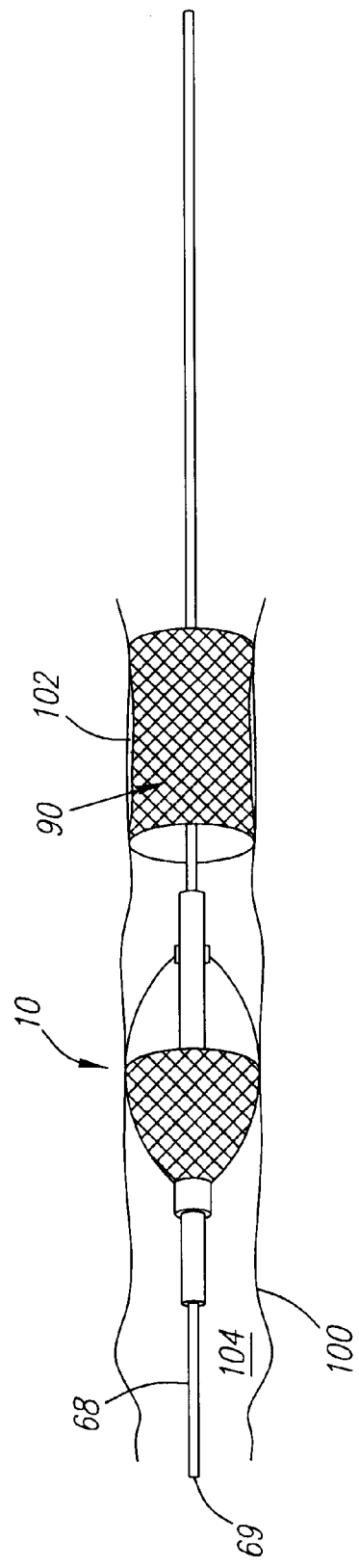
FIG. 2F is a cross-sectional view of the blood vessel of FIGS. 2A–2D, showing a stent implanted across the treatment site.

As shown in FIG. 2F, after or instead of the angioplasty procedure, a stent 90 may be implanted within the treatment site 102. For example, a balloon-expandable, a self-expanding, or a coiled-sheet stent may be placed on a delivery device, such as a catheter (not shown). The delivery device may be advanced over the guidewire 68, and the stent 90 deployed and expanded to substantially engage the treatment site 102 and hold the lumen of the vessel 100 substantially open. The delivery device may then be withdrawn, leaving the stent 90 in place.

During these procedures, embolic material (not shown) may break off or otherwise be released from the treatment site 102, travel downstream and enter the pocket 36 of the vascular filter 10 through the open proximal end 34. The vascular filter 10 thus may prevent emboli from traveling further downstream where it may damage the patient.

Turning to FIGS. 2G and 2H, a retrieval device 110 may be used to recover the vascular filter 10 after the procedure is completed. The retrieval device 110 generally includes an elongate tubular sheath 112 and an elongate retrieval member 114 slidably disposed therein. The sheath 110 may be the same sheath 52 as used for the delivery device 50 described above. Alternatively, a similarly constructed sheath 112 may be provided that includes a proximal end 116 with a handle 118, a distal end 120, and a lumen 122 extending between the proximal and distal ends 116, 120. The lumen 122 includes an opening 124 and has a diameter for receiving the vascular filter 10 therein in its collapsed condition.

The retrieval member 114 is a flexible or semi-rigid tubular body having a proximal end 126 with a handle 128, a distal end 130, and a guidewire lumen 132 extending between the proximal and distal ends 126, 130. The distal end 130 generally includes a connector for securing the vascular filter 10 to the retrieval member 114.

For example, as shown in FIG. 3, the connector may include an annular-shaped balloon or other inflatable member 134 disposed within an enlarged recess 136 in the distal end 130 of the retrieval member 114. The enlarged recess 136 preferably has a diameter larger than the proximal end 21 of the tubular member 12 of the vascular filter. The retrieval member 114 may include an inflation lumen 138 communicating with an interior 140 of the inflatable member 134. The inflation lumen 138 extends proximally to an inflation port 142 at the proximal end 126 of the retrieval member 114, as shown in FIGS. 2G and 2H. The inflation port 142 is connectable to a source of inflation media, such as saline, for inflating the inflatable member 134, as is known in the art.

Other connectors may be provided instead of the inflatable member 134. For example, a mechanical actuator (not shown) may be provided in the enlarged recess 136 of the retrieval member 114 that may be activated from the proximal end 126. Alternatively, the distal end 130 of the retrieval member 114 and the proximal end 21 of the tubular member 12 of the vascular filter 10 may include cooperating connectors (not shown) for securing the vascular filter 10 to the retrieval member 114, such as cooperating threads (not shown).

In a further alternative, gripping fingers (not shown) may be provided on the distal end 130 of the retrieval member 114 for grabbing the proximal end 21 of the vascular filter 10. The gripping fingers may be mechanically actuatable from the proximal end 126 of the retrieval member 114, or they may be flexible to allow them to be advanced over and engage the proximal end 21 of the tubular member 12. The proximal end 21 of the tubular member 12 may include slots, tabs, an annular groove and the like (not shown) that may facilitate securely grabbing the vascular filter 10 with the gripping fingers. Alternatively, the retrieval member may include a reducible collet or collar (not shown) that may be cynched down or otherwise contracted in diameter to grab the tubular member.

Returning to FIGS. 2G and 2H, the retrieval device 110 may be used to recover the vascular filter 10 from within the blood vessel 100. The retrieval device 110 may be advanced over the guidewire 68 until the distal end 130 of the sheath 112 is positioned adjacent the vascular filter 10. The distal end 130 of the retrieval member 114 may be advanced through the opening 124, and the vascular filter secured to the distal end 130. For example, the retrieval member 114 may be manipulated until the proximal end 21 of the tubular member 12 of the vascular filter 10 is received in the enlarged recess 136 in the distal end 130, the inflatable member 134 not being inflated. Once the proximal end 21 is received therein, the inflatable member 134 may be inflated, thereby constricting the recess 136 and frictionally engaging the outer surface 18 of the vascular filter 10.

The distal end 130 of the retrieval member 114 may then be withdrawn back into the lumen 122 of the sheath 112, thereby pulling the vascular filter 10 along with it. Preferably, as the vascular filter 10 enters the lumen 122, the struts 24 slidably engage the distal end 120 of the sheath 112 around the opening 124, thereby directing the struts 24 against the outer surface 18 of the tubular member 12, i.e., compressing the expandable frame 14 to its collapsed condition. This action closes the proximal end 34 of the filter material, thereby substantially trapping any embolic material in the pocket 36.

Once the vascular filter 10 is fully received in the sheath 112, the retrieval device 110 may be withdrawn from the patient. The guidewire 68 may be withdrawn, leaving the stent 90 in place, as shown in FIG. 2I.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A vascular filter, comprising:
   a tubular member having a proximal end and a distal end, and including a lumen for receiving a guidewire therethrough;
   an expandable frame attached to the tubular member, the expandable frame being capable of assuming a collapsed condition and an enlarged condition;
   a filter material attached to the expandable frame, the filter material having an open proximal end when the expandable frame assumes its enlarged condition; and
   a connector on the proximal end of the tubular member for detachably securing the vascular filter to a delivery device.

2. The vascular filter of claim 1, wherein the expandable frame is biased to assume its enlarged condition.

3. The vascular filter of claim 1, wherein the expandable frame comprises a plurality of struts, each strut having first and second ends, the first end of each strut being attached to the tubular member.

4. The vascular filter of claim 3, further comprising a collar slidable on the tubular member, the second end of each strut being attached to the collar.

5. The vascular filter of claim 3, wherein each of the struts includes an intermediate region biased to bow outward from the tubular member.

6. The vascular filter of claim 5, wherein the proximal end of the filter material is attached to the intermediate region.

7. The vascular filter of claim 1, wherein the tubular member comprises a substantially rigid tubular body.

8. The vascular filter of claim 1, wherein the tubular member comprises an articulated substantially rigid tube.

9. The vascular filter of claim 1, wherein the tubular member has a length of not more than about 5 cm.

10. An apparatus for filtering a blood vessel, comprising:
    a vascular filter including a tubular member, an expandable frame attached to the tubular member, the expandable frame being capable of assuming collapsed and enlarged conditions, and a filter material attached to the expandable frame;
    a tubular sheath having a proximal end, a distal end for insertion into a blood vessel, and a lumen having an opening at the distal end, the lumen having a size for slidably receiving the vascular filter therein when the expandable frame is in its collapsed condition; and
    an elongate retrieval member having a distal end deployable from the distal end of the tubular sheath, the retrieval member having a connector on its distal end for securing the tubular member thereto.

11. The apparatus of claim 10, further comprising an elongate bumper member insertable into the lumen of the tubular sheath, the bumper member including a distal end configured for advancing the vascular filter received in the lumen through the opening beyond the distal end of the tubular sheath.

12. The apparatus of claim 10, wherein the lumen comprises an enlarged distal lumen region having a length at least as long as a length of the tubular member.

13. The apparatus of claim 10, wherein the retrieval member comprises a tubular body having a lumen therein, the tubular body being insertable into the lumen of the tubular sheath.

14. The apparatus of claim 13, wherein the lumen of the tubular body comprises an enlarged recess adjacent its distal end having a size for receiving a proximal end of the tubular member therein.

15. The apparatus of claim 14, wherein the connector comprises an expandable member in the enlarged recess, the expandable member being expandable into the enlarged recess for engaging the proximal end of the tubular member received therein.

16. The apparatus of claim 14, wherein the connector comprises a mechanically actuated collar, the collar being actuable to reduce its diameter, thereby engaging the proximal end of the tubular member.

17. The apparatus of claim 10, wherein a proximal end of the tubular member and the distal end of the retrieval member include cooperating connectors.

18. A method for filtering a blood vessel during an endovascular procedure, the method comprising the steps of:
   providing a vascular filter including an expandable frame and filter material disposed on a tubular member, the expandable frame being constrained in a collapsed condition;
   placing a guidewire within a blood vessel across a treatment site to a location downstream thereof;
   advancing the tubular member over the guidewire to the location downstream of the treatment site;
   expanding the expandable frame to an enlarged condition across the blood vessel, the guidewire being slidable within the tubular member;
   performing an endovascular procedure at the treatment site, the vascular filter capturing embolic material released during the procedure;
   advancing a retrieval member endovascularly to the location downstream of the treatment site;
   securing the vascular filter to the retrieval member; and
   withdrawing the vascular filter and retrieval member from the blood vessel.

19. The method of claim 18, wherein the endovascular procedure comprises deploying a stent across the treatment site.

20. The method of claim 18, wherein the endovascular procedure comprises:
   advancing an expandable member endovascularly to the treatment site; and
   expanding the expandable member to dilate the treatment site.

21. The method of claim 18, wherein the endovascular procedure comprises an atherectomy procedure.

22. The method of claim 18, wherein one or more devices used during the endovascular procedure are advanced over the guidewire.

23. The method of claim 18, further comprising the step of directing the expandable frame to its collapsed condition before withdrawing the vascular filter and retrieval member from the blood vessel.

24. The method of claim 23, wherein the retrieval member comprises a tubular sheath having a lumen therein, and wherein the expandable frame is directed to its collapsed condition by withdrawing the vascular filter into the lumen of the tubular sheath.

25. The method of claim 24, wherein the expandable frame comprises a plurality of struts biased to assume the enlarged condition, and wherein the expandable frame is directed to its collapsed condition as the plurality of struts contact the tubular sheath around the lumen as the vascular filter is withdrawn into the lumen.

26. The method of claim 18, wherein the step of advancing the retrieval member comprises advancing the retrieval member over the guidewire.

27. The method of claim 18, wherein the step of securing the tubular member to the retrieval member comprises securing a proximal end of the tubular member with a connector on the retrieval member.

28. The method of claim 27, wherein the retrieval member comprises a recess in a distal end thereof, the connector comprises a reducible collar, and wherein the step of securing the proximal end of the tubular member to the retrieval member comprises:
   manipulating the retrieval member until the proximal end of the tubular member is received in the recess in the distal end of the retrieval member; and
   actuating the reducible collar to reduce its diameter to engage the proximal end of the tubular member.

29. The method of claim 27, wherein the retrieval member comprises a recess in a distal end thereof, and wherein the connector comprises an expandable member in the recess.

30. The method of claim 29, wherein the step of securing the proximal end of the tubular member to the retrieval member comprises:
   manipulating the retrieval member until the proximal end of the tubular member is received in the recess in the distal end of the retrieval member; and
   expanding the expandable member to engage the proximal end of the tubular member.

31. The method of claim 18, wherein a proximal end of the tubular member and a distal end of the retrieval member include cooperating connectors for securing the tubular member to the retrieval member.

32. The method of claim 18, wherein the step of providing a vascular filter comprises providing the vascular filter within a lumen of a tubular sheath, the tubular sheath constraining the expandable frame in its collapsed condition.

33. The method of claim 32, wherein the step of advancing the tubular member over the guidewire comprises advancing a distal end of the tubular sheath over the guidewire with the vascular filter disposed within the lumen.

34. The method of claim 33, wherein the expandable frame is biased to assume its enlarged condition, and wherein the step of expanding the expandable frame comprises deploying the vascular filter from the lumen beyond the distal end of the tubular sheath.

35. The method of claim 34, wherein the step of deploying the vascular filter comprises advancing a bumper member distally within the lumen, the bumper member pushing the vascular filter through an opening in the distal end of the tubular sheath.

* * * * *